United States Patent [19]

Lagrange et al.

[11] Patent Number: 5,178,637
[45] Date of Patent: Jan. 12, 1993

[54] TINCTORIAL COMPOSITION BASED ON 5,6-DIHYDROXYINDOLINES AND METHOD FOR DYEING KERATINOUS FIBRES

[75] Inventors: Alain Lagrange, Chatou; Bernadette Luppi, Sevran; Alex Junino, Livry-Gargan, all of France

[73] Assignee: L'Oreal, Paris, France

[21] Appl. No.: 707,130

[22] Filed: May 31, 1991

[30] Foreign Application Priority Data

May 31, 1990 [FR] France ................................ 90 06803

[51] Int. Cl.$^5$ .............................................. A61K 7/13
[52] U.S. Cl. .......................................... 8/405; 8/406; 8/407; 8/408; 8/409; 8/410; 8/416; 8/423; 8/429; 552/302; 548/508
[58] Field of Search ................... 8/405, 406, 407, 408, 8/409, 410, 416, 423, 429; 552/302; 548/508

[56] References Cited

U.S. PATENT DOCUMENTS

| | | | |
|---|---|---|---|
| 3,649,160 | 3/1972 | Kalopissis et al. | 8/409 |
| 3,867,094 | 2/1975 | Kalopissis et al. | 8/416 |
| 3,963,764 | 6/1976 | Kalopissis et al. | 8/416 |
| 3,977,825 | 8/1976 | Kalopissis et al. | 8/407 |
| 3,984,402 | 10/1976 | Kalopissis et al. | 8/416 |
| 3,989,447 | 11/1976 | Kalopissis et al. | 8/407 |
| 4,013,404 | 3/1977 | Parent et al. | 8/423 |
| 4,045,170 | 8/1977 | Kalopissis et al. | 8/407 |
| 4,595,765 | 6/1986 | Murphy | 548/508 |
| 4,750,908 | 6/1988 | Rosenbaum et al. | 8/405 |
| 4,776,857 | 10/1988 | Carroll et al. | 8/405 |
| 4,921,503 | 5/1990 | Anderson et al. | 8/405 |
| 5,011,500 | 4/1991 | Grollier et al. | 8/410 |
| 5,053,053 | 10/1991 | De Labbey et al. | 8/405 |

FOREIGN PATENT DOCUMENTS 1916139 11/1969 Fed. Rep. of Germany.
726078 3/1955 United Kingdom.

OTHER PUBLICATIONS

Mishra, S. N. et al, "Studies Related to the Chemistry of Melanins. Part III. Synthesis of 5,6-Dihydroxyindoline", J. Chem. Soc. (C), 1967, pp. 1424–1427.
Fichier Chemical Abstracts, vol. 107, No. 214088m.

Primary Examiner—A. Lionel Clingman
Assistant Examiner—William S. Parks
Attorney, Agent, or Firm—Jacobson, Price, Holman & Stern

[57] ABSTRACT

The invention relates to the use of a 5,6-dihydroxyindoline corresponding to the formula (I):

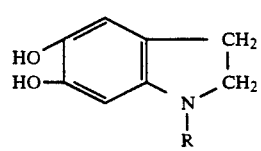

in which R represents a hydrogen atom or a $C_1$–$C_4$ alkyl group, as well as the acid addition salts of these compounds for dyeing keratinous materials, in particular human keratinous materials, and to the tinctorial compositions and methods employed.

27 Claims, No Drawings

TINCTORIAL COMPOSITION BASED ON 5,6-DIHYDROXYINDOLINES AND METHOD FOR DYEING KERATINOUS FIBRES

The present invention relates to the use of 5,6-dihydroxyindolines for dyeing keratinous fibres, in particular human keratinous fibres such as hair, to tinctorial compositions and to dyeing methods using these compounds.

It has already been proposed in the past to dye hair using, as couplers, specific monohydroxyindolines or monoaminoindolines, in particular in French Patent No. 2 008 797; U.S. Pat. No. 4,013,404 describes monoaminoindolines or diaminoindolines or monohydroxyindolines as oxidation base or as couplers, used in oxidation dyeing of hair.

Moreover, the dyes of the indole family, in particular 5,6-dihydroxyindole, are known for their use in dyeing keratinous fibres such as human hair, in particular from French Patents FR-A-1 133 594 and 1 166 172.

The Applicant has just discovered that, compared with the known 5,6-dihydroxyindole, 5,6-dihydroxyindolines, in particular in salt form, have particularly remarkable properties in respect of the stability on storage in the media customarily used in dyeing keratinous fibres.

Compared with 5,6-dihydroxyindole, these compounds also have a good solubility in water.

The inventors have found, moreover, that these compounds oxidise particularly readily in alkaline solution and may be used in hair dyeing without possibly using an oxidising agent, which permits a varied range of more or less deep shades to be obtained.

The subject of the invention is, therefore, the use of 5,6-dihydroxyindolines and their salts for dyeing keratinous fibres, in particular hair.

Another subject of the invention comprises the tinctorial compositions intended for dyeing keratinous fibres and in particular human hair and containing at least one 5,6-dihydroxyindoline.

Dyeing methods using these compounds are a further subject of the invention.

Other subjects of the invention will become apparent on reading the description and the examples which follow.

The 5,6-dihydroxyindolines used for dyeing keratinous fibres and in particular human keratinous fibres, such as hair, according to the invention, are essentially characterised in that they correspond to the formula:

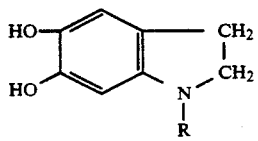

(I)

in which R represents a hydrogen atom or a $C_1$-$C_4$ alkyl group, and the acid addition salts of these compounds.

The preferred salts are the hydrochlorides or hydrobromides.

The preferred compounds used according to the invention are 5,6-dihydroxyindoline, 5,6-dihydroxyindoline hydrochloride, 5,6-dihydroxyindoline hydrobromide, N-ethyl-5,6-dihydroxyindoline, N-methyl-5,6-dihydroxyindoline and N-butyl-5,6-dihydroxyindoline.

Amongst these compounds, 5,6-dihydroxyindoline hydrobromide is particularly preferred.

The compounds of formula (I) in which R=H or a $C_1$-$C_4$ alkyl group are synthesised by demethylation of optionally N-alkylated 5,6-dimethoxyindole in the presence of HCl by heating at 140°-150° C. in a sealed tube as described in J. Chem. Soc. (C) 1424 (1967) SWAN or by heating under reflux in concentrated HBr under normal pressure.

The 5,6-dimethoxy-N-alkylindolines may be prepared either by conventional alkylation of 5,6-dimethoxyindoline using alkyl halide or dialkyl sulphate, or by reduction of dialkoxyindoles by sodium borohydride in the presence of a carboxylic acid, in accordance with the GRIBBLL method described in J.A.C.S. - 1974, 96, 7812.

The 5,6-dihydroxy-N-alkylindolines may be prepared by direct alkylation of 5,6-dihydroxyindoline, which may be synthesised by the SWAN method mentioned above.

5,6-Dihydroxyindoline hydrobromide is a new compound and is a subject of the invention. It is prepared by demethylation of 5,6-dimethoxyindole, the preparation of which is indicated above, using concentrated hydrobromic acid, with refluxing of the latter.

This compound is particularly stable on storage under the customary conditions for storage of tinctorial compositions for keratinous fibres.

The N-($C_2$-$C_4$)alkyl-5,6-dihydroxyindolines are new compounds, as well as their salts, and are another subject of the invention.

The 5,6-dihydroxyindolines of formula (I), defined above, are generally used with the aid of compositions which are another subject of the invention.

The tinctorial compositions intended to be used for dyeing keratinous fibres and in particular human keratinous fibres such as hair, according to the invention, are characterised in that they contain at least one 5,6-dihydroxyindoline corresponding to the formula (I) defined above, in a medium appropriate for dyeing.

The amount of 5,6-dihydroxyindoline(s) of formula (I) used in the composition is generally in proportions of 0.01 to 8% by weight relative to the total weight of the composition, and preferably of from 0.03 to 5% by weight.

These compositions may be in diverse forms, in particular in the form of more or less thickened lotions, creams, foams and gels, which may be packaged in the form of aerosols.

They may also be one element in a multicomponent dyeing agent placed in a multicompartment device or dyeing kit.

The medium appropriate for dyeing is preferably an aqueous medium which must be cosmetically acceptable when the compositions are intended to be used for dyeing living human hair. This aqueous medium may consist of water or a water/solvent(s) mixture.

The pH of the compositions is between 3 and 12.

The solvents are chosen from organic solvents and preferably from ethyl alcohol, propyl alcohol or isopropyl alcohol, tert-butyl alcohol, ethylene glycol, ethylene glycol monomethyl, monoethyl and monobutyl ethers, ethylene glycol monoethyl ether acetate, propylene glycol, propylene glycol and dipropylene glycol monomethyl ethers and methyl lactate.

The particularly preferred solvents are ethyl alcohol and propylene glycol.

The compounds according to the invention have the advantage of being able to be used in an essentially aqueous medium.

It is also possible to use a medium consisting of anhydrous solvents chosen from the solvents defined above. In this case, the composition is either mixed with an aqueous medium at the time of use or is applied to the keratinous fibres previously wetted with an aqueous composition.

According to the invention, a medium containing less than 1% of water is termed an anhydrous solvent medium.

When the medium appropriate for dyeing consists of a water/solvent(s) mixture, the solvents are used in concentrations of between 0.5 and 75% by weight relative to the total weight of the composition, and preferably in proportions of less than 20% by weight.

The compositions according to the invention may contain adjuvants customarily used for dyeing keratinous fibres and in particular cosmetically acceptable adjuvants when these compositions are applied for dyeing living human hair.

These compositions may contain, in particular, fatty amides in preferential proportions of 0.05 to 10% by weight, anionic, cationic, nonionic or amphoteric surfactants, or their mixtures, preferably present in proportions of between 0.1 and 50% by weight, thickeners, perfumes, sequestering agents, film-forming agents, treatment agents, dispersing agents, conditioners, preservatives, opacifying agents and agents for swelling keratinous fibres.

The thickeners are chosen from sodium alginate, gum arabic, guar gum, heterobiopolysaccharides, such as xanthan gum, scleroglucans, cellulose derivatives, such as methyl cellulose, hydroxyethyl cellulose, hydroxypropyl methyl cellulose or the sodium salt of carboxymethyl cellulose, and acrylic acid polymers, which are preferably crosslinked.

It is also possible to use inorganic thickeners, such as bentonite.

These thickeners are used on their own or as a mixture and are preferably present in proportions of between 0.1 and 5% by weight relative to the total weight of the composition, and advantageously of between 0.5 and 3% by weight.

The alkalinising agents which may be used in the compositions may be, in particular, amines, such as alkanolamines or alkylamines, or alkali metal or ammonium hydroxides or carbonates.

The acidifying agents which may be used in these compositions may be chosen from lactic acid, acetic acid, tartaric acid, phosphoric acid, hydrochloric acid and citric acid.

It is, of course, possible to use any other alkalinising or acidifying agent which is acceptable, in particular in the case of dyeing hair, in cosmetics.

When the compositions are used in the form of a foam, they may be packaged under pressure and in an aerosol device in the presence of a propellant and at least one foam generator.

The foam-generating agents may be anionic, cationic, nonionic or amphoteric foaming polymers, or their mixtures, or surfactants of the type of those defined above.

The method for dyeing keratinous fibres, in particular human keratinous fibres, which is another subject of the invention, is essentially characterised in that it consists in applying to these fibres a composition (A) defined above and containing at least one 5,6-dihydroxyindoline corresponding to the formula (I) defined above, in a medium appropriate for dyeing, in keeping the composition in contact with the fibres for a period sufficient to develop the colour, either in air or with the aid of an oxidising system, and in rinsing and optionally washing the fibres dyed in this way.

According to a first embodiment of the invention, dyeing of the fibres may be carried out without the addition of an external oxidising agent, solely in contact with the air.

According to another embodiment, the colour is developed with the aid of a chemical oxidising system chosen from:

(i) iodide ions and hydrogen peroxide, the composition (A) containing 5,6-dihydroxyindoline of formula (I) additionally comprising, in this case, either iodide ions or hydrogen peroxide, and the application of the composition (A) is preceded or followed by the application of a composition (B) which contains, in a medium appropriate for dyeing, either:
  (a) hydrogen peroxide at a pH of between 2 and 12 and preferably of between 2 and 7, when the composition (A) contains iodide ions, or:
  (b) iodide ions at a pH of between 3 and 11, when the composition (A) contains hydrogen peroxide;

(ii) the application of the composition (A) containing the 5,6-dihydroxyindoline of formula (I) being followed by the application of an aqueous composition (B) having an acid pH, the composition (A) or the composition (B) containing at least one nitrite;

(iii) oxidants chosen from hydrogen peroxide, periodic acid and its water-soluble salts, sodium hypochlorite, chloramine T, chloramine B, potassium ferricyanide, silver oxide, Fenton's reagent, lead-(IV) oxide, caesium sulphate and ammonium persulphate; these oxidants being present in the composition (A) containing the 5,6-dihydroxyindoline of formula (I) or being applied simultaneously or sequentially by means of a composition (B) containing them in a medium appropriate for dyeing;

(iv) metal anions chosen from permanganates or dichromates, these oxidising agents being applied by means of an aqueous composition (B), at a pH of 2 to 10, before the application of the composition (A);

(v) salts of metals of groups 3 to 8 of the periodic table, these metal salts being applied in a separate step by means of a composition (B) containing these salts in a medium appropriate for dyeing;

(vi) rare earth salts, these rare earth salts being applied by means of a composition (B) containing them in a medium appropriate for dyeing, the composition (B) being applied before or after the application of the composition (A) containing the 5,6-dihydroxyindoline of formula (I); and (vii) a quinone derivative chosen from ortho- or para-benzoquinones, ortho- or para-benzoquinone monoimines or diimines, 1,2- or 1,4-naphthoquinones, ortho- or para-benzoquinone sulphonimides, $\alpha,\omega$-alkylenebis-1,4-benzoquinones or 1,2- or 1,4-naphthoquinone monoimines or diimines, the 5,6-dihydroxyindoline of formula (I) and the quinone derivatives being chosen such that the difference in redox potential $\Delta E$ between the redox potential $E_i$ of the 5,6-dihydroxyindoline of formula (I) determined at pH 7 in a phosphate medium on a vitreous carbon electrode by means of voltammetry and the redox potential $E_q$ of the quinone derivative determined at pH 7 in a phosphate medium by polarography on a mercury electrode relative to the saturated calomel electrode is such that:

$$\Delta E = E_i - E_q \leqq 320 \text{ millivolts.}$$

According to a preferred embodiment of the invention, the application of the compositions (A) and (B) is separated by a step comprising rinsing with water.

According to a first variant of the dyeing method using oxidising systems, a composition (A) containing, in a medium appropriate for dyeing, at least one compound of formula (I) in combination with iodide ions is applied to the keratinous material, the application of the composition (A) being preceded or followed by the application of a composition (B) which contains hydrogen peroxide in a medium appropriate for dyeing.

This method may also be carried out by applying to the keratinous fibres at least one composition (A) containing, in a medium appropriate for dyeing, the compound of formula (I) in combination with hydrogen peroxide and having a pH of between 2 and 7 and preferably of between 3.5 and 7, the application of the composition (A) being preceded or followed by the application of a composition (B) which contains iodide ions in a medium appropriate for dyeing.

The iodide ion in this variant of the method is preferably chosen from alkali metal iodides, alkaline-earth metal iodides or ammonium iodide. The iodide is more particularly potassium iodide.

The iodide ions are present in the compositions (A) or (B) in proportions of generally between 0.007 and 4% by weight, expressed as $I^-$ ions, and preferably of between 0.08 and 1.5% by weight relative to the total weight of the composition (A) or (B).

According to a second variant, this method may be carried out using a nitrite as oxidising agent for developing the colouring. The nitrites which may be used more particularly in accordance with the invention are:

alkali metal nitrites, alkaline-earth metal nitrites or ammonium nitrite or the nitrite of any other cation which is cosmetically acceptable when it is used for dyeing living human hair;

organic derivatives of nitrites, such as, for example, amyl nitrite; and nitrite vectors, that is to say compounds which on conversion form nitrites of the type defined above.

The particularly preferred nitrites are sodium nitrite, potassium nitrite or ammonium nitrite.

This variant of the method is carried out by applying to the keratinous materials the composition (A) based on the compound of formula (I) defined above and then an aqueous acid composition (B), the composition (A) or (B) containing at least one nitrite.

The nitrites are generally used in proportions of between 0.02 and 1 mole/liter.

According to a third variant of this method, the oxidants are chosen from hydrogen peroxide, chloramine T, chloramine B, periodic acid and its water-soluble salts, sodium hypochlorite, potassium ferricyanide, silver oxide, Fenton's reagent, lead(IV) oxide, caesium sulphate and ammonium persulphate. These agents are preferably applied to the fibres by means of a composition (B) and after the application of the composition (A).

These oxidising agents are present in proportions sufficient to develop a colour and preferably in proportions of between 0.004 mole and 0.7 mole, in particular between 0.01 mole and 0.04 mole, per 100 g of composition.

According to a fourth variant of this process, in a first step a composition containing, in a medium appropriate for dyeing, at a pH of between 2 and 10, a metal anion having a good affinity for keratin and having a redox potential higher than that of the compounds of formula (I) is applied to the keratinous fibres. This anion is preferably chosen from permanganates or dichromates and more particularly potassium permanganate and sodium dichromate.

These metal anions are generally used in anion molalities of higher than $10^{-3}$ moles/1,000 g up to preferably 1 mole/1,000 g.

In a second step, a composition containing a compound corresponding to the formula (I) defined above in a medium appropriate for dyeing, at a pH of between 4 and 10, is applied.

The compositions containing the anions must not contain organic agents having a reducing effect on the anions.

According to a fifth variant of the invention, oxidation catalysts chosen from metal salts, such as manganese, cobalt, iron, copper and silver salts, are used.

By way of example, manganese sulphate, manganese lactate, cobalt chloride, ferric chloride, cupric chloride or ammoniacal silver nitrate may be used.

The preferred salts are the copper salts. These salts are used in proportions of 0.01 to 2%, expressed as metal ions, relative to the total weight of the composition used and containing these salts.

According to this variant, the keratinous fibres, in particular the hair, are brought into contact with a composition (B) containing the metal salt in a medium appropriate for dyeing, before or after the application of the composition (A) containing the compound of formula (I), and rinsing is preferably carried out between the two steps.

The preferred embodiment consists in applying a cupric salt in a first step and the composition (A) containing the 5,6-dihydroxyindoline of formula (I) in a second step.

This dyeing may be followed after rinsing by the application of a hydrogen peroxide solution in order to brighten the colour obtained if necessary.

According to a sixth variant, rare-earth salts are used. The rare-earth salts which can be used according to the invention are chosen from the lanthanide salts, and in particular the cerium $Ce^{3+}$, $Ce^{4+}$, lanthanum $La^{3+}$, europium $Eu^{2+}$, $Eu^{3+}$, gadolinium $Gd^{3+}$, ytterbium $Yb^{2+}$, $Yb^{3+}$, and dysprosium $Dy^{3+}$ salts. The preferred salts are in particular the sulphates, chlorides or nitrates.

These rare-earth salts are present in proportions of between 0.1 and 8% by weight relative to the total weight of the composition.

Cerium $Ce^{3+}$ and $Ce^{4+}$ salts in the form of sulphates and chlorides are preferably used.

According to a seventh variant, the composition containing the quinone derivative is applied before or after the composition (A) containing the compound of formula (I).

1,4-Benzoquinone may be mentioned as an example of a quinone derivative.

The concentration of quinone derivatives is preferably between 0.005 and 1 mole/liter in the composition (B). The pH of the composition (B) is between 2 and 10 and preferably below 7.

When compositions based on hydrogen peroxide are used in the various methods described above, the hydrogen peroxide content is generally between 1 and 40 volumes and preferably between 2 and 10 volumes and more particularly between 3 and 10 volumes.

The invention also relates to a multicomponent agent for colouring keratinous fibres and in particular human keratinous fibres, intended in particular to be used in the embodiment of the dyeing method defined above and using an oxidising system. In this case, the dyeing agent comprises at least two components, the first of which consists of the composition (A) defined above and containing the 5,6-dihydroxyindoline of formula (I) and the other component consists of one of the compositions (B) also defined above.

The respective components (A) and (B) are chosen depending on the different variants of the method explained above.

The invention also relates to a multicompartment device or "dyeing kit" or "dyeing set" containing all of the components intended to be applied in a single dyeing to the keratinous fibres by single or successive applications with or without premixing as mentioned above.

Such devices are known per se and may comprise a first compartment containing the composition (A) containing the 5,6-dihydroxyindoline of formula (I) in a medium appropriate for dyeing, and, in a second compartment, a composition (B) of the type defined above and containing the oxidising agent.

The multicompartment devices which can be used according to the invention may be fitted with means for mixing at the time of use and their contents may be packaged under an inert atmosphere.

When the medium containing the 5,6-dihydroxyindoline of formula (I) is anhydrous, a third compartment may be provided which contains an aqueous medium appropriate for dyeing and intended to be mixed just before use with the composition in the first compartment.

The 5,6-dihydroxyindoline of formula (I), the compositions and the method according to the invention may be used to dye natural or already dyed hair, which may or may not have been permanent-waved and may or may not have been straightened, or highly or slightly bleached hair which may have been permanent-waved.

It is also possible to use them for dyeing fur or wool.

The examples are intended to illustrate the invention without, however, having a limiting character.

PREPARATION EXAMPLE 1

Preparation of 5,6-dihydroxyindoline hydrobromide

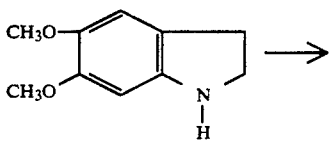

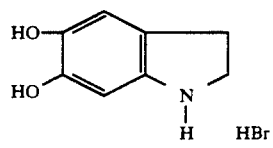

97.8 g of 5,6-dimethoxyindoline are dissolved in 400 ml of 47% hydrobromic acid and the solution is refluxed for four hours. The hydrobromic acid is evaporated under reduced pressure and the residue is taken up in 0.5 l of ethanol and treated with active charcoal under ethanol reflux for 30 minutes and the mixture is then filtered through celite. A volume of ethyl ether is then added progressively to the cooled filtrate. 94.8 g of 5,6-dihydroxyindoline hydrobromide are obtained.

Yield = 75%

Pale beige.

|  | Analysis | | | | |
| --- | --- | --- | --- | --- | --- |
|  | C | H | Br | N | O |
| Calculated | 41.40 | 4.34 | 34.43 | 6.04 | 13.79 |
| Found | 41.57 | 4.37 | 34.36 | 5.97 | 13.94 |

PREPARATION EXAMPLE 2

Preparation of N-butyl-5,6-dihydroxyindoline hydrobromide.

1st step

Preparation of N-butyl-5,6-dimethoxyindoline 30 g (0.17 mole) of 5,6-dimethoxyindoline are dissolved in 300 ml of dimethoxyethane in the presence of 10.8 g (0.17 mole) of KOH and 500 mg of tetrabutylammonium hydrogen sulphate.

18 ml (0.17 mole) of bromobutane are added rapidly and the mixture is refluxed for 5 hours. The reaction mixture is then poured into water. After extraction with methylene chloride and evaporation of the solvent, a colourless liquid is obtained which is purified by chromatography on silica gel, using methylene chloride as eluent.

27.6 g of N-butyl-5,6-dimethoxyindoline are obtained in the form of a colourless liquid.

2nd step

Preparation of N-butyl-5,6-dihydroxyindoline hydrobromide 5 g (0.02 mole) of N-butyl-5,6-dimethoxyindoline in 50 ml of 48% hydrobromic acid are refluxed for 3 hours.

The solution is evaporated to dryness and the residue, dissolved in 100 ml of absolute ethanol in the presence of vegetable black, is refluxed for 30 minutes.

After filtering through celite and concentrating under vacuum, the product is recrystallised from absolute ethanol.

3.5 g of N-butyl-5,6-dihydroxyindoline hydrobromide are obtained in the form of light brown crystals.

Bromide content determined = 3.31 meq/g

Theory: 3.47 meq/g.

PREPARATION EXAMPLE 3

Preparation of N-ethyl-5,6-dihydroxyindoline (hydrobromide)

4.5 g (0.02 mole) of N-ethyl-5,6-dimethoxyindoline in 40 ml of 48% hydrobromic acid are refluxed for 3 hours.

The solution is evaporated to dryness and the residue, dissolved in 80 ml of absolute ethanol in the presence of vegetable black, is refluxed for 30 minutes.

After filtering through celite and concentrating under vacuum, the product is precipitated by the addition of ethyl ether.

4.7 g of N-ethyl-5,6-dihydroxyindoline hydrobromide are obtained in the form of an orange-yellow solid.

Bromide content determined = 3.87 meq/g
Theory: 3.84 meq/g.

EXAMPLE 1

| | |
|---|---|
| 5,6-Dihydroxyindoline hydrobromide | 2.0 g |
| Ethyl alcohol | 15.0 g |
| Potassium iodide | 1.0 g |
| Preservatives, qs | |
| Demineralised water qs | 100.0 g |

This composition is applied for 15 minutes to grey hair which is 90% white. After rinsing, an oxidising milk at pH 3 assaying 12.5 volumes of hydrogen peroxide is applied for 5 minutes.

The hair is rinsed, shampooed and dried.

A deep brown colouring is finally obtained.

EXAMPLE 2

The following composition is prepared:

| COMPOSITION (A2) | |
|---|---|
| 5,6-Dihydroxyindoline hydrobromide | 2.3 g |
| 96° ethyl alcohol | 10.0 g |
| Hydroxyethyl cellulose sold under the name NATROSOL 250 HHR by AQUALON | 1.0 g |
| Glycoside alkyl ether sold as product containing 60% of AS under the name TRITON CG 110 by ROHM & HAAS | 5.0 g AS |
| Triethanolamine qs pH 5.7 | |
| Demineralised water qs | 100.0 g |

This composition (A) is applied to grey hair which is 90% white for 10 minutes.

After rinsing, the following composition (B) is applied:

| COMPOSITION (B2) | |
|---|---|
| 20 volume hydrogen peroxide | 66.0 g |
| 20% ammonia | 6.3 g |
| Water qs | 100.0 g |

After having allowed this composition (B) to remain on the hair for 10 minutes, the hair is rinsed, washed and then dried. The hair is coloured golden ash blond.

EXAMPLE 3

The composition (A2) described in Example 2 is applied for 10 minutes to permanent-waved grey hair. After rinsing, the following composition (B) is applied:

| COMPOSITION (B3) | |
|---|---|
| 20 volume hydrogen peroxide | 33.0 g |
| Aqueous solution containing 8% of monoethanolamine qs | 100.0 g |

This composition is applied for 10 minutes, after which the hair is rinsed, washed and then dried. The hair is coloured in an ash chestnut shade.

EXAMPLE 4

| COMPOSITION (A4) | |
|---|---|
| 5,6-Dihydroxyindoline hydrobromide | 1.6 g |
| 96° ethyl alcohol | 10.0 g |
| Hydroxyethyl cellulose sold under the name NATROSOL 250 HHR by AQUALON | 1.0 g |
| Glycoside alkyl ether sold as product containing 60% of AS under the name TRITON CG 110 by ROHM & HAAS | 5.0 g AS |
| Triethanolamine qs pH 6.5 | |
| Water qs | 100.0 g |

This composition is applied for 15 minutes to grey hair which is 90% white. After rinsing, the following composition (B4) is applied:

| COMPOSITION (B4) | |
|---|---|
| Sodium metaperiodate | 5.0 g |
| HCl qs pH 3 | |
| Water qs | 100.0 g |

After having allowed this composition to remain on the hair for 15 minutes, the hair is rinsed, washed and then dried. The hair is dyed golden light chestnut.

EXAMPLE 5

| COMPOSITION (B5) | |
|---|---|
| Copper sulphate pentahydrate | 1.0 g |
| Sodium lauryl sulphate sold under the name SIPON LCS98 by HENKEL | 1.0 g |
| Monoethanolamine qs pH 9 | |
| Water qs | 100.0 g |

This composition is applied for 5 minutes to permanent-waved grey hair. After rinsing, the following composition (A5) is applied:

| COMPOSITION (A5) | |
|---|---|
| 5,6-Dihydroxyindoline hydrobromide | 0.78 g |
| 96° ethyl alcohol | 10.0 g |
| Hydroxypropyl cellulose sold under the name KLUCEL G by AQUALON | 2.0 g |
| Glycoside alkyl ether sold as product containing 60% of AS under the name TRITON CG 110 by ROHM & HAAS | 2.1 g AS |
| Oxyethylenated nonylphenol containing 9 moles of ethylene oxide | 0.1 g |
| Tartaric acid | 0.3 g |
| Triethanolamine qs pH 8.5 | |
| Water qs | 100.0 g |

After having allowed this composition to remain on the hair for 10 minutes, the hair is rinsed and then dried. The hair is coloured ash brown.

EXAMPLE 6

The composition (A5) described in Example 5 is applied for 10 minutes to permanent-waved grey hair. After rinsing and drying, the hair is dyed golden light grey.

EXAMPLE 7

| COMPOSITION (A7) | |
|---|---|
| 5,6-Dihydroxyindoline hydrobromide | 1.6 g |

COMPOSITION (A7)

| | |
|---|---|
| 96° ethyl alcohol | 10.0 g |
| Potassium iodide | 0.8 g |
| Hydroxyethyl cellulose sold under the name NATROSOL 250 HHR by AQUALON | 1.0 g |
| Glycoside alkyl ether sold under the name TRITON CG 110 by ROHM & HAAS | 5.0 g AS |
| Sodium lauryl ether sulphate | 0.2 g AS |
| Triethanolamine qs pH 6.5 | |
| Water qs | 100.0 g |

This composition is applied to grey hair which is 90% white for 15 minutes. After rinsing, a 12.5 volume hydrogen peroxide solution is applied for 5 minutes. After rinsing, washing and drying, the hair is coloured dark ash blond.

EXAMPLE 8

A 2.5% solution of 5,6-dihydroxyindoline hydrobromide in a 90/10 aqueous alcoholic medium is prepared. This solution is allowed to remain in contact with a lock of hair which is 90% white for 15 minutes at ambient temperature. The hair is rinsed and rubbed dry and the colouring is then developed using a 60/40 aqueous alcoholic solution contain 2% of 1,4-benzoquinone.

The solution is left on the hair for 8 minutes.

After rinsing, shampooing, rinsing and drying, a black colour is obtained.

The redox potential values are:

$E_i = 100$ mV  $E_q = 10$ mV  $\Delta E = 90$ mV.

EXAMPLE 9

COMPOSITION (A9)

| | |
|---|---|
| N-Butyl-5,6-dihydroxyindoline | 0.5 g |
| Hydroxyethyl cellulose sold under the name NATROSOL 250 HHR by AQUALON | 1.0 g |
| Ethyl alcohol | 10.0 g |
| Glycoside alkyl ether sold under the name TRITON CG 110 by ROHM & HAAS | 5.0 g AS |
| Triethanolamine qs pH 5 | |
| Water qs | 100.0 g |

COMPOSITION (B9)

| | |
|---|---|
| 20 volume hydrogen peroxide | 66.0 g |
| Aqueous solution containing 8% of monoethanolamine | 33.0 g |

The solution (A9) is applied to hair which is 90% white for 10 minutes. After rinsing, the solution (B9) is applied for 10 minutes. After rinsing, washing and drying, the hair is coloured blue-green.

EXAMPLE 10

Composition (A10)

This is similar to composition (A9), in which the 0.5 g of N-butyl-5,6-dihydroxyindoline is replaced by 1 g of N-methyl-5,6-dihydroxyindoline.

Composition (B10)

This is identical to composition (B9).

The dyeing conditions are identical to those described for Example 9.

The hair is coloured matt golden ash.

EXAMPLE 11

Composition (A11)

This is similar to composition (A9), in which the 0.5 g of N-butyl-5,6-dihydroxyindoline is replaced by 1 g of N-ethyl-5,6-dihydroxyindoline.

Composition (B11)

This is identical to composition (B9).

The dyeing conditions are identical to those of Example 9.

The hair is coloured blue-green.

EXAMPLE 12

| | |
|---|---|
| N-Methyl-5,6-dihydroxyindoline | 0.5 g |
| Ethyl alcohol | 10.0 g |
| Hydroxypropyl cellulose sold under the name KLUCEL G by AQUALON | 2.0 g |
| Glycoside alkyl ether sold under the name TRITON CG 110 by ROHM & HAAS | 1.2 g AS |
| Oxyethylenated nonylphenol containing 9 moles of ethylene oxide | 0.1 g |
| Tartaric acid | 0.3 g |
| Triethanolamine | 3.75 g |
| Demineralised water qs | 100.0 g |
| The pH is 8.5. | |

This composition is applied to grey hair which is 90% white for 10 minutes.

After rinsing, the hair is dried. This composition is applied twice in succession, after which the hair is coloured matt blue-grey.

EXAMPLE 13

| | |
|---|---|
| N-Ethyl-5,6-dihydroxyindoline | 1.0 g |
| Ethyl alcohol | 10.0 g |
| Potassium iodide | 1.0 g |
| Hydroxyethyl cellulose sold under the name NATROSOL 250 HHR by AQUALON | 1.0 g |
| Glycoside alkyl ether sold under the name TRITON CG 110 by ROHM & HAAS | 5.0 g AS |
| Sodium lauryl ether sulphate | 0.2 g AS |
| Triethanolamine qs pH 5 | |
| Water qs | 100.0 g |

This composition is applied to grey hair which is 90% white for 15 minutes.

After rinsing, a 12.5 volume hydrogen peroxide solution is applied for 5 minutes.

After rinsing, washing and drying, the hair is coloured light ash blond.

EXAMPLE 14

This is similar to Example 13, in which the 1 g of N-ethyl-5,6-dihydroxyindoline is replaced by 1 g of N-methyl-5,6-dihydroxyindoline.

The dyeing conditions are those described in Example 13. The hair is coloured matt golden ash.

EXAMPLE 15

This is similar to Example 13, in which the 1 g of N-ethyl-5,6-dihydroxyindoline is replaced by 0.5 g of N-butyl-5,6-dihydroxyindoline.

The dying conditions are those of Example 13. The hair is coloured blue-green.

We claim:

1. A tinctorial composition useful for dyeing keratinous fibres, in particular human keratinous fibers, comprising from 0.01 to 8% by weight, relative to the total weight of the composition, of at least one 5,6-dihydroxyindoline corresponding to the formula (I):

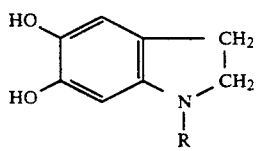

in which R represents a hydrogen atom or a $C_1$–$C_4$ alkyl group, or an acid addition salt thereof in a medium suitable for dyeing.

2. A composition according to claim 1, wherein the 5,6-dihydroxyindoline is present in the composition in proportions of between 0.03 and 5% by weight relative to the total weight of the composition.

3. A composition according to claim 1, wherein the medium suitable for dyeing is an aqueous medium of water or a water/solvent mixture.

4. A composition according to claim 3, wherein the solvent is ethyl alcohol, propyl alcohol, isopropyl alcohol, tert-butyl alcohol, ethylene glycol, ethylene glycol monomethyl ether, ethylene glycol monoethyl ether, ethylene glycol monobutyl ether, ethylene glycol monoethyl ether acetate, propylene glycol, propylene glycol monomethyl ether, dipropylene glycol monomethyl ether or methyl lactate.

5. A composition according to claim 1, wherein the composition contains a fatty amide, anionic, cationic, nonionic or amphoteric surfactant, or a mixture thereof, thickener, perfume, sequestering agent, film-forming agent, treatment agent, dispersing agent, conditioner, preservative, opacifying agent or agent for swelling keratinous fibre, or a mixture thereof.

6. A composition according to claim 1, wherein the pH of the composition is between 3 and 12.

7. A method for dyeing keratinous fibres, in particular human keratinous fibres, wherein at least one composition as defined in claim 4 is applied to these fibres, this composition is kept in contact with the fibres for a period sufficient to develop a colour, ether in air or with the aid of an oxidizing system, and wherein the fibres are then rinsed.

8. A method according to claim 7, wherein the colour is allowed to develop in contact with air without adding an external oxidizing agent.

9. A method according to claim 7, wherein the at least one composition as defined in claim 1 is identified as composition (A) and the colour is developed with the aid of a chemical oxidising system consisting of:

(i) iodide ions and hydrogen peroxide, the composition (A) additionally containing, in this case, either (a) iodide ions or (b) hydrogen peroxide and the application of the composition (A) being preceded or followed by the application of a composition (B) which contains, in a medium appropriate for dyeing, either:
  (a) hydrogen peroxide at a pH of between 2 and 12 when the composition (A) contains iodide ions, or
  (b) iodide ions at a pH of between 3 and 11, when the composition (A) contains hydrogen peroxide;

(ii) nitrite, the application of the composition (A) being followed by the application of an aqueous composition (B) having an acid pH, the composition (A) or the composition (B) containing at least one nitrite;

(iii) oxidant comprising hydrogen peroxide, periodic acid or a water-soluble salt thereof, sodium hypochlorite, chloramine T, chloramine B, potassium ferricyanide, silver oxide, Fenton's reagent, lead-(IV) oxide, caesium sulphate or ammonium persulphate; the oxidant being present in the composition (A) or being applied simultaneously or sequentially by means of a composition (B) containing it in a medium appropriate for dyeing.

(iv) metal anions comprising permanganate or dichromate, the oxidising agent being applied by means of an aqueous composition (B), at a pH of 2 to 10, before application of the composition (A);

(v) salt of a metal of groups 3 to 8 of the periodic table, the metal salt being applied in a separate step by means of a composition (B) containing the salt in a medium appropriate for dyeing;

(vi) rare-earth salt, the rare-earth salt being applied by means of a composition containing the salt in a medium appropriate for dyeing, the composition (B) being applied before or after the application of the composition (B) being applied before or after the application of the composition (A); and (vii) a quinone derivative comprising an ortho- or para-benzoquinone, an ortho- or para-benzoquinone monoimine or diimine, a 1,2- or 1,4-naphthoquinone, an ortho- or para-benzoquinone sulphonimide, an $\alpha,\omega$-alkylenebis-1,4-benzoquinone or a 1,2- or 1,4-naphthoquinone monoimine or diimine, the 5,6-dihydroxyindoline of formula (I) and the quinone derivative being selected such that the difference in redox potential $\Delta E$ between the redox potential $E_1$ of the 5,6-dihydroxyindoline of formula (I) determined at pH 7 in a phosphate medium on a vitreous carbon electrode by means of voltammetry and the redox potential $E_q$ of the quinone derivative determined at pH 7 in a phosphate medium by polarography on a mercury electrode relative to the saturated calomel electrode such that:

$$\Delta E = E_i - E_q \leq 320 \text{ millivolts;}$$

the composition (B) being applied before or after the application of the composition (A).

10. A method according to claim 9, wherein composition (A) in combination with iodide ions is applied to the keratinous fibres, the application of the composition (A) being preceded or followed by the application of the composition (B) which contains hydrogen peroxide in a medium appropriate for dyeing.

11. A method according to claim 9, wherein at least one composition (A) in combination with hydrogen peroxide and having a pH of between 2 and 7 is applied to the keratinous fibres, the application of the composition (A) being preceded or followed by the application of the composition (B) which contains iodide ions in a medium appropriate for dyeing.

12. A method according to claim 10, wherein the iodide ions are present in the composition (A) or (B) in a proportion of between 0.007 and 4% by weight, expressed as $I^-$ ions, relative to the total weight of the composition (A) or (B).

13. A method according to claim 9, wherein composition (A) is applied to the keratinous fibres and an acid aqueous composition (B) is then applied, the composition (A) or the composition (B) containing at least one nitrite comprising alkali metal nitrite, alkaline-earth metal nitrite or ammonium nitrite or the nitrite of any other cosmetically acceptable cation, an organic nitrite derivative or a nitrite vector generating a nitrite of the type define above.

14. A method according to claim 13, wherein the nitrite is present in a proportion of between 0.02 and 1 mole/liter.

15. A method according to claim 9, wherein composition (B) containing, at a pH of between 2 and 10, a metal anion having a good affinity for keratin fibers and comprising permanganate or dichromate is applied to the keratinous fibres and, in a second step, the composition (A) is applied at a pH or between 4 and 10.

16. A method according to claim 15, wherein the permanganate or dichromate is used in an anion molality of higher than $10^{-3}$ moles/1,000 g up to 1 mole/1,000 g and the compositions do not contain an organic agent having a reducing effect on the anions.

17. A method according to claim 9, wherein composition (A) is applied to the keratinous fibres and composition (B), containing a metal salt comprising a manganese, cobalt, iron, copper or silver salt, is applied before or after the composition (A).

18. A method according to claim 17, wherein the metal salt is used in a proportion of between 0.01 and 2% by weight, expressed as metal ions, relative to the total weight of the composition.

19. A method according to claim 9, wherein composition (A) is applied and, before or after this composition, composition (B) containing a rare-earth salt selected from the group consisting of a cerium, lanthanum, europium, gadolinium, ytterbium and dysprosium salt is applied.

20. A method according to claim 19, wherein a the rare-earth salt is present in a proportion of between 0.1 and 8% by weight relative to the total weight of the composition.

21. A method according to claim 9, wherein a composition based on hydrogen peroxide is used as the oxidizing medium, the hydrogen peroxide content in the composition being between 1 and 40 volumes.

22. A multicomponent agent for dyeing keratinous fibres, in particular human keratinous fibres, comprising a first component consisting of a composition (A) containing a 5,6-dihydroxyindoline corresponding to formula (I):

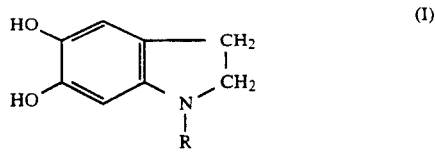

in which R represents a hydrogen atom or a $C_1$-$C_4$ alkyl group, or an acid addition salt thereof, and a second component consisting of a composition (B) which contains, in a medium appropriate for dyeing, either:
  (a) hydrogen peroxide at a pH of between 2 and 12 when the composition (A) contains iodide ions, or
  (b) iodide ions at a pH of between 3 and 11, when the composition (A) contains hydrogen peroxide.

23. A multicompartment device or "dyeing kit", comprising different compartments containing different components of the dyeing agent defined in claim 22.

24. A composition according to claim 1, wherein the salt is the hydrochloride or hydrobromide.

25. A composition according to claim 1, wherein 5,6-dihydroxyindoline is 5,6-dihydroxyindoline, 5,6-dihydroxyindoline hydrochloride, 5,6-dihydroxyindoline hydrobromide, N-ethyl-5,6-dihydroxyindoline, N-methyl-5,6-dihydroxyindoline or N-butyl-5,6-dihydroxyindoline.

26. A method according to claim 21, wherein the hydrogen peroxide content in the composition is between 2 and 10 volumes.

27. A tinctorial composition according to claim 1, wherein the 5,6-dihydroxyindoline is 5,6-dihydroxyindoline hydrochloride, an N-($C_2$-$C_4$)alkyl-5,6-dihydroxyindoline or a salt of the latter.

28. New compound consisting of 5,6-dihydroxyindoline hydrobromide.

29. New compounds consisting of N-($C_2$-$C_4$)alkyl-5,6-dihydroxyindolines and their salts.

* * * * *

Adverse Decision In Interference

Patent No. 5,178,637, Alain Lagrange, Bernadette Luppi, Alex Junino, TINCTORIAL COMPOSITION BASED ON 5,6-DIHYDROXYINDOLINES AND METHOD FOR DYEING KERATINOUS FIBRES, Interference No. 103,548, final judgment adverse to the patentees rendered June 29, 2001, as to claims 1-29.

*(Official Gazette October 30, 2001)*